US008093782B1

(12) United States Patent
Hossack

(10) Patent No.: US 8,093,782 B1
(45) Date of Patent: Jan. 10, 2012

(54) SPECIALIZED, HIGH PERFORMANCE, ULTRASOUND TRANSDUCER SUBSTRATES AND RELATED METHOD THEREOF

(75) Inventor: John A. Hossack, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 299 days.

(21) Appl. No.: 12/191,839

(22) Filed: Aug. 14, 2008

Related U.S. Application Data

(60) Provisional application No. 60/964,668, filed on Aug. 14, 2007.

(51) Int. Cl.
*A61B 18/00* (2006.01)

(52) U.S. Cl. .......................... 310/327; 310/326; 600/452

(58) Field of Classification Search .................. 310/326, 310/327; 600/452
See application file for complete search history.

(56) References Cited

U.S. PATENT DOCUMENTS

| | | | | |
|---|---|---|---|---|
| 4,869,768 | A | 9/1989 | Zola | |
| 5,297,553 | A | 3/1994 | Sliwa, Jr. et al. | |
| 6,225,475 | B1 * | 5/2001 | Legloahec et al. | 549/233 |
| 6,258,034 | B1 * | 7/2001 | Hanafy | 600/459 |
| 2004/0249060 | A1 * | 12/2004 | Hucke et al. | 524/589 |
| 2005/0043625 | A1 * | 2/2005 | Oliver et al. | 600/459 |
| 2006/0184035 | A1 * | 8/2006 | Kimura et al. | 600/466 |
| 2007/0016053 | A1 * | 1/2007 | Lo et al. | 600/459 |

OTHER PUBLICATIONS

Girard et al., "High element count two dimensional tranducer array," IEEE Symposium on Ultrasonics, 964-967 (2003).

Eames et al., "Investigation of Low Glass Transition Temperature Epoxy Resin Blends for Lossy, yet Machinable, Transducer Assemblies," Ultrasonics Symposium 2007, IEEE, 1921-1924 (2007).

* cited by examiner

*Primary Examiner* — Walter Benson
*Assistant Examiner* — Bryan Gordon
(74) *Attorney, Agent, or Firm* — McDonnell Boehnen Hulbert & Berghoff LLP

(57) ABSTRACT

Backing substrates for reducing parasitic echoes produced within a ultrasonic transducer are provided comprising a polymeric material, for example, an epoxy having a glass transition temperature ($T_g$) ranging from about 10 to 50° C.; or an epoxy having an acoustical attenuation that increases by at least about 2 dB/mm at 5 MHz in a temperature range of about 5° C. to 40° C. Transducer assemblies comprising the backing substrates and methods for producing the assemblies are also provided.

21 Claims, 1 Drawing Sheet

SPECIALIZED, HIGH PERFORMANCE, ULTRASOUND TRANSDUCER SUBSTRATES AND RELATED METHOD THEREOF

CROSS-REFERENCE TO RELATED APPLICATIONS

This application claims the benefit of the filing date, under 35 USC §119(e), of U.S. Provisional Application Ser. No. 60/964,668, filed Aug. 14, 2007, which is hereby incorporated by reference in its entirety.

STATEMENT OF GOVERNMENT FUNDING

The invention described herein was made in part with government support under grant number NIBIB R01EB0002349, awarded by the National Institutes of Health. The United States Government has certain rights in the invention.

FIELD OF THE INVENTION

The invention relates to transducer arrays for diagnostic or therapeutic ultrasound, and backing substrates capable of attenuating interfering echoes caused by operation of the array.

BACKGROUND OF THE INVENTION

Ultrasound is the most widely used diagnostic modality in the world (with the possible exception of traditional X-ray). There remains a need for improved transducer performance. In this context, the transducer active material, usually but not always piezoelectric, is supported on a substrate that dissipates ultrasound energy that is propagated into it. (Only ultrasound energy emanating from the front of the transducer is desirable since it propagates into the tissue.) The backscattered ultrasound signals are received by the same transducer array, converted to electrical signals and processed in attached beamformer electronic hardware.

Conventional transducer backing blocks comprise a blend of various subsets of: polymer (usually, but not always an epoxy), fibers (or short fiber segments), particulate fillers (usually metal powders or metal oxides—such as $Al_2O_3$ or $SiO_2$), bubbles (such as free gas, glass or polymer microballoons) and sometimes "rubberizing" agents such as modifiers (plasticizers) appropriate for the polymer used.

Frequently, the electrical "signal" connections to each of array elements is made on the back surface of the transducer—since there is more space there than on the front surface where a very short path between the active transducer material and the tissue is required. The electrical connections are sometimes made using IC die wirebonding techniques (thermal or ultrasonically induced gold wire bonds) or using a thin polyimide (or similar) flexible circuit with plated (e.g. gold) copper traces that align with the transducer elements. In the context of highly complex designs—such as a 2D array—it becomes practically impossible to design a flexible circuit to provide the necessary signal line "fan-out". Wirebonding techniques become highly problematic.

Commercially available Printed Circuit Board (PCB) materials (used as the substrate in a transducer, and containing the copper traces) can provide a low cost method of fanning out the element traces from the array to connectors (or to "front end" ICs such as protection circuits, pre-amplifiers, digitizers, etc,), however, the materials within the PCBs have insufficient attenuation and parasitic echoes are received from within the PCB and from the reflective surface at the back of the PCB. Typically, the PCBs are filled with woven glass fiber that is potted in a polymer—possibly a polyester polymer—though the exact composition of the polymer is immaterial to the current discussion and is rarely described in detail. Since the primary application of commercial PCB materials is as substrates for Printed Circuit Assemblies (PCAs) that are frequently subject to solder reflow oven processes, the polymer is chosen to have a glass transition temperature that is sufficiently high (~200° C.) to avoid excess geometric distortion during solder reflow. ("Reflow" is the process by which previously placed solder "tinned" components are permanently attached by way of "reflow" melting the adjacent solder surfaces on both the component "legs" and the PCB solder tinned "pads").

Therefore there exists a need in the art to provide backing block materials which can improve transducer performance through increased attenuation of parasitic echoes generated within the devices during their operation.

BRIEF SUMMARY OF INVENTION

In a first aspect, the invention provides transducer assemblies comprising an ultrasonic transducer mounted to a backing substrate, wherein the backing substrate comprises a polymeric material having a glass transition temperature ($T_g$) ranging from about 10 to 50° C.

As used herein an "ultrasonic transducer" is a device capable of producing a sound having a frequency between about 500 kHz and 20 MHz, and preferably, between about 1 and 20 MHz, and more preferably, between about 5 and 10 MHz.

In a second aspect, the invention provides transducer assemblies comprising a ultrasonic transducer mounted to a backing substrate, wherein the backing substrate comprises a polymeric material having an acoustical attenuation that increases by at least about 2 dB/mm at 5 MHz in a temperature range of about 5° C. to 40° C. As is well known, attenuation is a function of frequency—being substantially higher at higher frequencies. The rate of increase of attenuation is a function of the particular material in question. Where not otherwise stated, approximately 5 MHz is the frequency of interest in this specification when referencing values for acoustical attenuation.

In a third aspect, the invention provides backing substrates for an ultrasonic transducer having one or more layers, wherein at least one layer comprises a polymeric material having a glass transition temperature ($T_g$) ranging from about 10 to 50° C.

In a fourth aspect, the invention provides backing substrates for an ultrasonic transducer having one or more layers, wherein at least one layer comprises a polymeric material having an acoustical attenuation that increases by at least about 2 dB/mm at 5 MHz in a temperature range of about 5° C. to 40° C.

In a fifth aspect, the invention provides methods for preparing an ultrasonic transducer assembly comprising mounting an ultrasonic transducer to a front surface of a backing substrate having the front and a back surface, wherein the backing substrate comprises a polymeric material having a glass transition temperature ($T_g$) ranging from about 10 to 50° C.

In a sixth aspect, the invention provides methods for preparing an ultrasonic transducer assembly comprising mounting an ultrasonic transducer to a front surface of a backing substrate having the front and a back surface, wherein the backing substrate comprises a polymeric material having an acoustical attenuation that increases by at least about 2 dB/mm at 5 MHz in a temperature range of about 5° C. to 40° C.

Briefly, the present invention involves the careful choice of polymer for the backing substrate material. Normally, a high glass transition temperature ($T_g$) is required to maximize dimensional stability throughout manufacturing and to assure maximum transducer operating lifetime in the face of probably mechanical shocks (such as floor drops). For an embodiment of this invention, we select a $T_g$ that is relatively close to room temperature and/or body temperature, taking account of the frequency dependence of $T_g$ as is familiar to one skilled in the art, so that the glass transition is the selected temperature range for the frequencies of interest—typically 1-20 MHz.

As used herein, the "glass transition temperature" ($T_g$) refers to the temperature below which a non-crystalline solid (i.e., an amorphous solid), solidifies (i.e., becomes glassy). More specifically, it defines a pseudo second order phase transition in which a supercooled melt yields, on cooling, a glassy structure and properties similar to those of crystalline materials e.g. of an isotropic solid material.

Some exemplary and non-limiting novel elements associated with various embodiments of the present invention may include, but not limited to, use of low $T_g$ polymer for ultrasound transducer backing and/or use of a chilled manufacturing process to deliberately take the transducer substrate from a soft state to a hard state and thus enabling manufacture.

One advantage of the various embodiments may be related to low-cost, two-dimensional (2D) ultrasound arrays where there is a need for a low-cost, yet high attenuating, backing substrate.

DETAILED DESCRIPTION OF THE INVENTION

Figure 1:
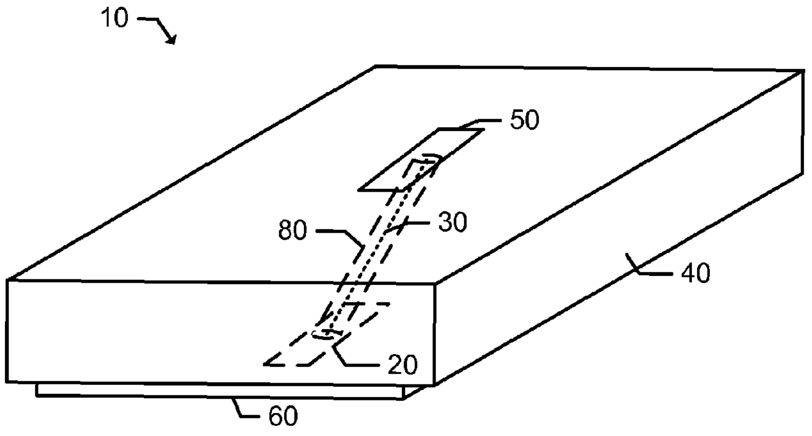
FIG. 1 is an example embodiment of a printed circuit board from an oblique view.

In one embodiment of the transducer assemblies and backing substrates of the invention, the polymeric material comprises an organic polymer. In another embodiment, the polymeric material comprises an epoxy (e.g., a cross-linked epoxy), polyimide, polyester, phenolic resin, polyvinyl chloride, polyvinyl acetate, or polystyrene. Examples of epoxies include, but are not limited to those having repeat units derived from 2,2'-(4,4'-(propane-2,2-diyl)bis(4,1-phenylene))bis(oxy)bis(methylene)dioxirane (DER 332, Electron Microscopy Sciences (EMS), Hatfield, Pa., USA), polypropylene glycol diglycidyl ether (DER 736, Electron Microscopy Sciences (EMS), Hatfield, Pa., USA), or mixtures thereof. In one particular example, the epoxy comprises repeat units derived from DER 332, and DER 736 (i.e., 2,2'-(4,4'-(propane-2,2-diyl)bis(4,1-phenylene))bis(oxy)bis(methylene)dioxirane:polypropylene glycol diglycidyl ether) in a ratio of about 0.75-1.25:1.25-0.75, or 0.80-1.20:1.20-0.80; or 0.85-1.15:1.15-0.85, or 0.90-1.10:1.10-0.90; or 0.95-1.05:1.05-0.95; or about 0.75:1.25, or about 0.80:1.20, or about 0.85:1.15, or about 0.90:1.10; or about 0.95:1.05, or about 1:1, or about 1.05:0.95, or about 1.10:0.90, or about 1.15:0.85, or about 1.20:0.80, or about 1.25:0.75. In certain embodiments, the epoxy comprises repeat units derived from DER 332, and DER 736 in a ratio of about 1:1. The epoxies can further comprise a cross-linking agent, such as, but not limited to dodecenyl succinic anhydride (DDSA).

In another example, epoxies include, but are not limited to those having repeat units derived from Ciba-Geigy resins such as Araldite™ CY-208 (diglycidylether of polypropylene glycol, CAS RN#9072-62-2) and/or Araldite™ MY-753 with an appropriate hardener, such as Araldite™ HY-756.

In other embodiments of the transducer assemblies and backing substrates of the invention, the polymeric material further comprises a plasticizer. While no specific plasticizer (for reducing $T_g$ of the backing substrate) is required in the invention, the plasticizer can be any such material known to one skilled in the art which is compatible (e.g., miscible) with the one or more polymers comprising the backing substrate. Examples of plasticizers include, but are not limited to phthalates, trimellitates, adipates, sebacates, maleates, benzoates, sulfonamides, organophosphates, glycols, polyalkylene glycol esters, acetylated monoglycerides, polymeric plasticizers, and mixtures thereof.

In one embodiment, when present, the phthalate plasticizer comprises one or more dialkyl phthalates, wherein each alkyl group is independently a branched or linear alkyl chain having 1-12 carbon atoms. For example, phthalate plasticizers include but are not limited to bis(2-ethylhexyl) phthalate, diisononyl phthalate, bis(n-butyl) phthalate, butyl benzyl phthalate, diisodecyl phthalate, di(n-octyl) phthalate, diisooctyl phthalate, diethyl phthalate, diisobutyl phthalate, di(n-hexyl)phthalate, and mixtures thereof.

As used herein, the term "alkyl" refers to a straight or linear hydrocarbon chain containing 1-12 atoms. Examples of alkyl include, but are not limited to methyl, ethyl, propyl, isopropyl, butyl, t-butyl, hexyl, 2-ethylhexyl, octyl, nonyl, decyl, undecyl, and dodecyl.

In another embodiment, when present, the trimellitate plasticizer comprises one or more trialkyl trimellitates, wherein each alkyl group is independently a branched or linear alkyl chain having 1-12 carbon atoms. For example, trimellitate plasticizers include but are not limited to trimethyl trimellitate, tri(2-ethylhexyl) trimellitate, decyl dioctyl trimellitate, didecyl octyl trimellitate, heptyl dinonyl trimellitate, diheptyl nonyl trimellitate, tri(n-octyl) trimellitate, and mixtures thereof.

In another embodiment, when present, the adipate plasticizer comprises one or more monoalkyl or dialkyl adipates, wherein each alkyl group is independently a branched or linear alkyl chain having 1-12 carbon atoms. For example, adipate plasticizers include but are not limited to bis(2-ethylhexyl) adipate, dimethyl adipate, monomethyl adipate, dioctyl adipate, and mixtures thereof.

In another embodiment, when present, the sebacate plasticizer comprises one or more monoalkyl or dialkyl sebacate, wherein each alkyl group is independently a branched or linear alkyl chain having 1-12 carbon atoms. For example, sebacate plasticizers include but are not limited to dibutyl sebacate.

In another embodiment, when present, the maleate plasticizer comprises one or more dialkyl maleate, wherein each alkyl group is independently a branched or linear alkyl chain having 1-12 carbon atoms. For example, maleate plasticizers include but are not limited to dibutyl maleate, diisobutyl maleate, and mixtures thereof.

In another embodiment, when present, the sulfonamide plasticizer comprises one or more N-alkyl phenylsulfonamide (i.e., Ph-S(O)$_2$N(H)R), wherein the alkyl group (R) is independently a branched or linear alkyl chain having 1-12 carbon atoms, wherein the phenyl (Ph) is optionally substituted with one or more methyl groups and the alkyl is optionally substituted with hydroxyl. For example, N-alkyl phenylsulfonamide plasticizers include but are not limited to N-ethyl toluenesulfonamide, N-(2-hydroxypropyl) benzenesulfonamide, N-(n-butyl) benzenesulfonamide, and mixtures thereof.

In another embodiment, when present, the organophosphate plasticizer comprises a trisubstituted phosphate of the formula, $(O{=}){P}(OR^1)_3$, wherein each $R^1$ group is independently a branched or linear alkyl chain having 1-12 carbon atoms or a phenyl group optionally substituted by a $C_1$-$C_4$ alkyl group. For example, trisubstituted phosphate plasticizers include but are not limited to tricresyl phosphate, tributyl phosphate, and mixtures thereof.

In another embodiment, when present, the polyol ester plasticizer comprises a dialkanoyl oligoethylene glycol, wherein each alkanoyl group independently comprises $—C(O)R^2$, wherein each $R^2$ is independently a branched or linear alkyl chain having 1-12 carbon atoms and the oligoethylene glycol comprises 2-10 ethylene glycol repeat units (i.e., $R^2C(O)—O(CH_2CH_2O)_n—C(O)R^2$, where n is 2-10, and each $R^2$ is independently as defined previously). For example, dialkanoyl oligoethylene glycol plasticizers include but are not limited to triethylene glycol dihexanoate, tetraethyleneglycol diheptanoate, and mixtures thereof.

In the preceding embodiments, the polymeric material can be designed so that it is machinable (i.e., hard) at chilled temperatures (e.g., 0° C.-8° C.), but becomes acoustically lossy when at the transducer's operating temperature (20° C.-40° C.).

In one example, this can be achieved by selecting the polymeric material, for example the blend ratio of the epoxies or the inclusion of one or more plasticizers, to produce a glass transition temperature ($T_g$) at about 10-50° C. (e.g., approximately 40° C.). A polymeric material is considered machinable when it can be machined (e.g., with a saw, mill or drill) without tearing out pieces larger than that actually being cut by the cutting tool edge. Further, the polymeric material should be machined at a temperature where the material is not too brittle; therefore, should a polymeric material present issues with brittleness due to, for example, high incorporation of physical cross-links, then the polymeric material can be warmed to a temperature (below the $T_g$) which allows for machining thereof; alternatively, the polymeric material may be reformulated to decrease the $T_g$.

In another example, suitable polymeric materials for the backing substrates have an acoustical attenuation increase of at least about 2 dB/mm, or at least at about 5 dB/mm, or at least about 10 dB/mm at 5 MHz in a temperature range of about 5° C. to 40° C. Acoustical attenuations at 5 MHz are measured as described in the examples below. For example, the polymeric materials of the backing substrate can have an acoustical attenuation increase of about 2-100 dB/mm, or 5-100 dB/mm. or 10-100 dB/mm, or 2-50 dB/mm, or 5-50 dB/mm, or 10-50 dB/mm, or 2-10 dB/mm. or 2-5 dB/mm at 5 MHz in a temperature range of about 5° C. to 40° C.

Further, in any of the preceding embodiments, the backing substrate can further comprise a filler material. Examples of filler materials include, but are not limited to, glass fibers, glass particles, metal (in powder, particulate or fiber (including fiber short segment) form) (e.g., tungsten), metal oxide powders (e.g., silica and/or alumina), and mixtures thereof. Filled backing substrates can have an acoustical attenuation increases of, for example, about 2-100 dB/mm, or 5-100 dB/mm. or 10-100 dB/mm, or 2-50 dB/mm, or 5-50 dB/mm, or 10-50 dB/mm, or 2-30 dB/mm. or 5-30 dB/mm, or 10-30 dB/mm at 5 MHz in a temperature range of about 5° C. to 40° C.

In certain embodiments, the backing substrate is a printed circuit board (PCB) 40 having a circuit layer formed over one or more substrate layers, wherein at least one substrate layer comprises the polymeric material as described above. Such printed circuit boards may be multi-layered PCBs having a plurality of substrate layers as are well-known in the art, provided at least one layer of the PCB comprises the polymeric material as described above. The remaining layers can comprise materials typically encountered in PCB design, for example, polyimide, polyester, or epoxy composite material optionally containing filler materials, such as glass fibers or cotton paper, to provide rigidity to the PCB, onto which metal interconnect circuits (e.g., gold, silver, aluminum, or copper) are overlayed. For example, the PCB may comprise a flexible PCB such as a flexible polyimide PCB (commonly referred to as "flex circuit"). In certain embodiments, the substrate layer, comprising the polymeric material as described above, is in contact with the circuit layer.

The PCBs 40 may have one or more metal pads (20,50) formed on the faces thereof to allow surface mounting of electronic elements, such as transducer elements or circuitry elements (infra), to the PCB 40. For example, a PCB 40, as described above, having a front and back surface can have metal pads (20,50) formed on the front and back surfaces thereof, wherein each metal pad 50 on the front surface is in electrical communication with a metal pad 20 formed on the back surface. Electrical communication between the pads can be accomplished by electrical interconnecting layers of the PCB as are familiar to those skilled in the art.

Figure 2:
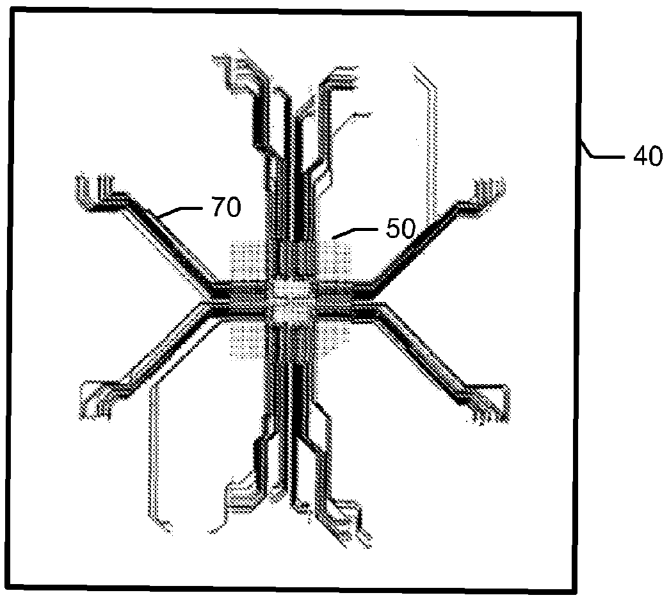
FIG. 2 is an example embodiment of a printed circuit board from an overhead view; all arranged in accordance with at least some embodiments of the present disclosure.

Transducer assemblies and backing substrates (see, for example, Girard E, Zhou S, Walker W, Blalock T, Hossack J. High element count two dimensional transducer array. 2003 IEEE Symposium on Ultrasonics. Pages 964-967, which is hereby incorporated by reference), comprising a PCB 40 as described above and as shown in FIG. 2, can provide a method of fanning out the element traces 70 from the array to connectors 50—or to "front end" ICs (i.e. protection circuits, pre-amplifier, digitizer, etc.) in addition to providing improved performance with respect to attenuation of parasitic echoes produced by operation of the transducer.

In other embodiments, the backing substrate comprises one or a plurality of metal wires 30 encompassed by the polymeric material. Such wires 30 may comprise any metal suitable for making electrical interconnects, such as but not limited to gold, silver, copper, and aluminum. The metal wires 30 may be straight through the backing substrate, or they may enable fan-out to external connections. For example, straight through wires 30 may comprise plain holes 80 through the backing substrate with conductions on their surfaces (or filled). Such backing substrates may further comprise one or more metal pads (20,50) (e.g., gold, silver, tin, or copper) formed on the faces thereof to allow surface mounting of electronic elements, such as transducer elements or circuitry elements (infra), wherein each metal pad 50 on the front surface is in electrical communication with a metal pad 20 formed on the back surface via one or more of the metal wires 30 within the backing substrate.

In another embodiment, the transducer assemblies comprise a circuitry die comprising elements to operate the ultrasonic transducer 60, in contact with the backing substrate, wherein the backing substrate comprises one or a plurality of through holes 80 and the circuitry die is in electrical communication with the ultrasonic transducer through one or more metal interconnects 30 via the through holes 80. The inner surfaces of the through holes 80 can be coated with a metal, such as gold, silver, tin, or copper. The one or more metal interconnects 30 can be pins. Alternatively, the through holes 80 can be filled with a metal, such as gold, silver, tin, or copper.

In another embodiment, the transducer assemblies 60 comprise a circuitry die comprising elements to operate the ultrasonic transducer, in contact with the backing substrate, wherein the backing substrate comprises one or a plurality of through holes 80 and the circuitry die is in electrical communication with the ultrasonic transducer through one or more metal interconnects 30 via the through holes 80. The inner surfaces of the through holes 80 can be coated or filled with a metal, such as gold, silver, tin, or copper. The metal interconnects 30 can comprise one or more metal pads (20,50) (e.g., gold, silver, tin, or copper) formed on the front and back surface thereof to allow surface mounting of electronic elements, such as transducer elements or circuitry elements (infra), wherein each metal pad on the front surface 50 is in electrical communication with a metal pad 20 formed on the back surface via one or more of the metal coated or filled through-holes.

The backing substrates can have a thickness chosen to maximize assembly performance with respect to weight and bulk. For example, the backing substrates can have a thickness ranging from about 1 mm to about 20 mm; or from about 1 mm to about 10 mm; or from about 1 to 5 mm. In certain embodiments where a substrate with increased flexibility is desired, the backing substrate can have a thickness of less than about 1 mm (e.g., about 0.1-1.0 mm). Further, the backing substrates generally have a lateral extent which essentially matches or exceeds that of device assembled thereon (e.g., an ultrasonic piezoelectric array).

Any of the preceding transducer assemblies can be potted, for example, by enveloping 5 of the 6 faces of the assembly in a potting polymer familiar to those in the electronics industry, such as an epoxy or polystyrene, such that a face of the transducer remains exposed.

The transducer assemblies can further comprise an integrated heater positioned to heat the ultrasonic transducer to an operating temperature. The integrated heater can comprise, for example, resistive heating wires or ultrasonic heaters. The transducers are typically operated at or above room temperature to about mammalian body temperature (e.g., 37-40° C.). In fact, the operating temperature of transducers, internal to the device, may be several degrees warmer. Thus, there exists a window for operating the transducer above $T_g$ (where acoustic attenuation is high) but also not impractically removed from temperatures that are achievable with modest care during manufacture.

In certain embodiments, the ultrasonic transducer can be an piezoelectric transducer, for example, a piezoelectric ceramic (e.g., barium titanate, lead titanate, lead zirconate titanate (PZT), potassium niobate, lithium niobate, lithium tantalite, sodium tungstate, $Ba_2NaNb_5O_5$, $Pb_2KNb_5O_{15}$, sodium potassium niobate, and/or bismuth ferrite.) having metal contact layers (e.g., gold layers) on opposing faces of the layer.

In other embodiments, the transducer may be non piezoelectric—such a silicon MEMS based device such as one comprising an electrostatically operated silicon nitride membrane suspended above a grounded silicon substrate.

Further, in any of the preceding embodiments, the $T_g$ of the polymeric material of the backing substrate can be about 10° C. to 40° C.; or about 25° C. to 40° C.; or about 25° C. to 37° C.; or about 30° C. to 40° C. or about 35° C. to 40° C.; and/or the backing substrate attenuates a transmitted ultrasonic sound pulse by about 1-4 dB/mm. In another particular example, the backing substrate can attenuates a transmitted 5 MHz ultrasonic sound pulse by about 1-4 dB/mm.

Additional, very significant, gains in attenuation may be achieved by loading the backing substrate, for example, an epoxy, with a filler material, as described above, and in particular, tungsten or the glass fiber material typically encountered in PCBs. In one particular example, a transducer assembly is provided wherein the echoes produced by the backing substrate, comprising a filler material, when the ultrasonic transducer assembly is operated at an operating temperature of about 37° C., are attenuated by at least 3 dB/mm, or at least 10 dB/mm, for example, about 3-50 dB/mm, or about 3-30 dB/mm, or about 10-50 dB/mm, or about 10-30 dB/mm.

Any of the preceding ultrasonic transducer assemblies of the invention can be prepared according to a method comprising mounting an ultrasonic transducer to a front surface of a backing substrate having the front and a back surface, wherein the backing substrate comprises a polymeric material as described above. Mounting of electrical components herein can be accomplished with the use of a conductive adhesive, for example, a silver epoxy adhesive according to methods familiar to those skilled in the art. Alternatively, unfilled (electrically non conducting) adhesive may be used if point-point contact through the adhesive layer is achieved by way of extremely thin bond line.

The backing substrate can be any of the substrate described previously. For example, backing substrate can comprise (i) one or a plurality of metal wires encapsulated by the polymeric material; (ii) the polymeric material having one or a plurality of through holes from the front surface to the back surface of the backing substrate, or (iii) a printed circuit board (PCB) having a circuit layer formed over one or more substrate layers, wherein at least one of the substrate layers comprises the polymeric material, as described above.

Printed circuit boards (PCB) having a circuit layer formed over one or more substrate layers, wherein at least one of the substrate layers comprises the polymeric material as described above can be prepared, for example, by forming a metal layer over the backing substrate followed by masking and etching or milling to remove excess metal according to methods known to those skilled in the art to produce the circuit layer (i.e., a patterned circuit layer).

A backing substrate having one or a plurality of through holes from the front surface to the back surface of the backing substrate, as described previously, can be prepared by drilling the one or a plurality of through holes from a front surface to a back surface of the backing substrate, for example with drill bits made of solid tungsten carbide; alternatively, the through holes may be formed via laser ablation. The inner surfaces of the through holes can be coated with a metal, for example, silver, tin, nickel, or gold via immersion or electroless coating techniques familiar to those skilled in the art.

In one embodiment, the ultrasonic transducer can be mounted to the front surface of the backing substrate having one or a plurality of through holes from the front surface to the back surface of the backing substrate, as described previously, and a circuitry die comprising elements to operate the ultrasonic transducer, can be mounted to the back surface of the backing substrate. For example, the ultrasonic transducer can comprise one or more pins that are inserted into the one or more through holes.

In another embodiment, the ultrasonic transducer can be mounted to the front surface of a backing substrate having metal pads (e.g., gold, silver, tin, or copper) on the front and the back surfaces thereof, as described above, wherein the transducer is in electrical communication with at least one metal pad on the front surface and a circuitry die comprising elements to operate the ultrasonic transducer, can be mounted to the back surface of the backing substrate, where the circuitry die is in contact with at least one metal pad on the back surface. As discussed above, the metal pads on the back surface are in electrical communication with the metal pads on the front surface via, either wires within the backing substrate, or when the backing substrate is a PCB, as discussed above, via interconnects through one or more layers of the PCB.

In another embodiment, the ultrasonic transducer can be mounted to the backing substrate by depositing a first metal layer over the front face of the backing substrate; depositing an ultrasonic ceramic layer over the first metal layer; and depositing a second metal layer over the ultrasonic ceramic layer. Alternatively, an ultrasonic transducer element having a metal (e.g., gold) contact layer can be surface mounted to front surface of the backing substrate.

Such assemblies can be diced through the ultrasonic transducer to at least the backing substrate at one or a plurality of predetermined positions to form, for example, a 2-D transducer array.

During manufacture, the entire manufacturing process, a portion of the manufacturing process, the assemblies, or at least the backing substrate, can be chilled to below the $T_g$. Preferably, the backing substrate can be maintained at a temperature of about −40° C. to 20° C.; or about −20° C. to 20° C.; or about −10° C. to about 5° C. The chilling may be accomplished by placing the manufacturing steps in a chilled space or by refrigerating the dicing saw coolant/lubricant (usually water based) used. Among the several manufacturing processes, the element dicing process is the one of primary concern with respect to device reliability during manufacture. Therefore, the dicing saw can be placed in a chilled space (such as a commercial size refrigerator or freezer) or (less effectively but much cheaper) the dicing saw coolant/lubricant can be chilled using a chilling heat exchanger or ice cubes. Only those steps involving maximum risk need be chilled—or all manufacturing steps can be in chilled space.

As discussed previously, after manufacturing, the normally 6 sided transducer assembly can be supported by a rigid encapsulant (i.e., potted) on 5 sides—i.e. all sides except the front active face. Since, the device is supported on 5 out of 6 sides, the assemblies are robust even during later use when it reaches or exceeds the $T_g$ of the backing substrate.

The transducer assemblies of the invention can be used in conjunction with all existing imaging modes—B-Mode, C-Mode, 3D, all forms of Doppler, harmonic modes, with and without contrast agents. Further, the devices, systems and methods of various embodiments of the invention disclosed herein may utilize aspects disclosed in the following patents and publications: U.S. Pat. No. 4,869,768, entitled, “Ultrasonic transducer arrays made from composite piezoelectric materials”; U.S. Pat. No. 5,297,553, entitled, “Ultrasound transducer with improved rigid backing”; U.S. Pat. No. 6,258,034, entitled, “Apodization methods and apparatus for acoustic phased array aperture for diagnostic medical ultrasound transducer”; and US Pat. Appl. Pub. No. US 2007/00160534 A1, entitled “Ultrasonic Monitor with an Adhesive Member,” each of which are hereby incorporated by reference in their entirety.

Further, as necessary during operation, the transducer assemblies of the invention can go through a process to heat it up quickly from ambient temperature to body temperature. There are several approaches: (1) operating the transducer in a high energy mode—such a using high duty factor pulses simply to deliver energy to the piezoelectric and cause heating by way of acoustic loss and heating as a byproduct of <100% conversion efficiency; (2) Place fine wires through the backing substrate and passing a current to cause local heating; and/or (3) using integrated heating elements such as transducer materials: PZTs, other piezoelectric materials—single crystal PZN:PTs etc., silicon “cMUT” transducers, etc.

EXAMPLES

Example 1

Five epoxy blend ratios were formulated using DER 332 and DER 736 (Electron Microscopy Sciences (EMS), Hatfield, Pa., USA), hard and soft epoxy resins, respectively. A cross-linking agent (DDSA, Fluka/Riedel-de Haën, Seelze, Germany) and accelerator (DMP-30, EMS) were used to cure the epoxy samples. The blend ratios that were formed were: 4:0, 3:1, 2:2, 1:3, and 0:4 (ratio of DER 332:DER 736) Three thicknesses were made of each blend. One-way pitch-catch experiments were performed in a water tank at 7° C., 25° C., and 37° C. for each of the fifteen samples. The transmit pulse was centered at 5 MHz for all experiments. Attenuation per unit length was then calculated and verified by comparing the received signal amplitude between samples of differing thickness. (see, for example, Eames et al., “Investigation of Low Glass Transition Temperature Epoxy Resin Blends for Lossy, yet Machinable, Transducer Assemblies” Ultrasonics Symposium, 2007, IEEE 2007, page 1921-1924 (ISSN: 1051-0117), which is hereby incorporated by reference in its entirety).

The 1:1 (DER 332:DER 736) epoxy blend ratio yielded the most consistent and promising results. At a temperature of 7° C., the calculated attenuation was 1.3 dB/mm; at 25° C. the attenuation was 1.9 dB/mm; and at 37° C. the attenuation was 3.3 dB/mm. For a proposed transducer design, incorporating a 2 mm PCB (prepared from the 1:1 epoxy and comprising a filler, such as fiberglass or tungsten), the backing block echoes when operating at 37° C. may be attenuated by an additional 13 dB with respect to attenuation at the chilled temperature (7° C.).

Example 2

FIG. 1 is an example transducer and substrate apparatus for use with some embodiments of the present disclosure. The apparatus 10 may include a backing substrate made of a polymeric material comprising an organic polymer and transducer assemblies 60 comprising circuitry dies. In some embodiments, the backing substrate is a printed circuit board (PCB) 40 having a circuit layer formed over one or more substrate layers. Additionally, the apparatus 10 may include elements to operate the ultrasonic transducer assemblies 60, in contact with the backing substrate, wherein the backing substrate comprises one or a plurality of through holes 80 and the circuitry die is in electrical communication with the ultrasonic transducer through one or more metal interconnects 30 via the through holes 80. The apparatus 10 may also include metal pads formed on the front 50 and metal pads formed on the back 20 surfaces of the backing substrate.

In summary, an aspect of the various embodiments of the present invention relates to improved transducer backing materials that have the properties of being compatible with high channel count electrical termination, being low cost and having adequate acoustic attenuation even when used in a thin section. An aspect of the various embodiments of the present invention may provide, but not limited thereto, diagnostic and therapeutic ultrasound.

An advantage associated with various embodiments provide, among other things, an improved transducer backing materials that has the properties of being compatible with high channel count electrical termination, being low cost and having adequate acoustic attenuation even when used in a thin section.

The preceding patents, applications and publications as listed throughout this document are hereby incorporated by reference in their entirety herein.

I claim:

1. A transducer assembly comprising an ultrasonic transducer mounted to a backing substrate, wherein the backing substrate comprises a polymeric material having a glass transition temperature ($T_g$) ranging from about 10 to 50° C., and wherein the polymeric material has an acoustical attenuation that increases by at least about 2 dB/mm when the temperature of the backing substrate increases from about 5° C. to 40° C.

2. The transducer assembly of claim 1, wherein the polymeric material comprises an epoxy, polyimide, polyester, phenolic resin, polyvinyl chloride, polyvinyl acetate, or polystyrene.

3. The transducer assembly of claim 2, wherein the polymeric material comprises an epoxy comprising repeat units derived from 2,2'-(4,4'-(propane-2,2-diyl)bis(4,1-phenylene))bis(oxy)bis(methylene)dioxirane, polypropylene glycol diglycidyl ether, or mixtures thereof.

4. The transducer assembly of claim 3, wherein the epoxy further comprises a cross-linking agent.

5. The transducer assembly of claim 1, wherein the backing substrate further comprises a filler material.

6. The transducer assembly of claim 1, wherein the backing substrate is a printed circuit board (PCB) having a circuit layer formed over one or more substrate layers, wherein at least one of the substrate layers comprises the polymeric material having a glass transition temperature ($T_g$) ranging from about 10 to 50° C.

7. The transducer assembly of claim 1, comprising a circuitry die comprising elements to operate the ultrasonic transducer, in contact with the backing substrate, wherein the backing substrate comprises one or a plurality of through holes and the circuitry die is in electrical communication with the ultrasonic transducer through one or more metal interconnects via the through holes.

8. The transducer assembly of claim 7 wherein the metal interconnects comprise one or more metal pads on the front and back surfaces of the backing substrate, wherein each metal pad on the front surface is in electrical communication with a metal pad on the back surface via the through holes wherein the through holes are coated or filled with a metal.

9. The transducer assembly of claim 1, wherein the ultrasonic transducer is an piezoelectric ultrasonic transducer.

10. The transducer assembly of claim 1, wherein the $T_g$ of the polymeric material is about 25-40° C.

11. A backing substrate for an ultrasonic transducer having one or more layers, wherein at least one layer comprises a polymeric material having a glass transition temperature ($T_g$) ranging from about 10 to 50° C., and wherein the polymeric material has an acoustical attenuation that increases by at least about 2 dB/mm when the temperature of the backing substrate increases from about 5° C. to 40° C.

12. The backing substrate of claim 11, wherein the backing substrate is a printed circuit board (PCB) having a circuit layer formed over one or more substrate layers, wherein at least one of the substrate layers comprises the polymeric material having a glass transition temperature ($T_g$) ranging from about 10 to 50° C.

13. The backing substrate of claim 11 having one or a plurality of through holes from a front to a back surface of the backing substrate, wherein the inner surfaces of the through holes are optionally coated with a metal.

14. The backing substrate of claim 11, wherein the polymeric material comprises an epoxy, polyimide, polyester, phenolic resin, polyvinyl chloride, polyvinyl acetate, or polystyrene.

15. The backing substrate of claim 14, wherein the epoxy comprises repeat units derived from 2,2'-(4,4'-(propane-2,2-diyl)bis(4,1-phenylene)) bis(oxy)bis(methylene)dioxirane, polypropylene glycol diglycidyl ether, or a mixture thereof.

16. The backing substrate of claim 11, wherein the polymeric material further comprises a filler material.

17. The backing substrate of claim 11, wherein the $T_g$ of the polymeric material is about 25-40° C.

18. A method for preparing an ultrasonic transducer assembly comprising mounting an ultrasonic transducer to a front surface of a backing substrate having the front and a back surface, wherein the backing substrate comprises a polymeric material having a glass transition temperature ($T_g$) ranging from about 10 to 50° C., and wherein the polymeric material has an acoustical attenuation that increases by at least about 2 dB/mm when the temperature of the backing substrate increases from about 5° C. to 40° C.

19. The method of claim 18 comprising maintaining the backing substrate at a temperature below the $T_g$ of the polymeric material.

20. The method of claim 18, wherein at least a portion of the manufacturing process is maintained at a temperature ranging from about −40° C. to 20° C.

21. A transducer assembly comprising an ultrasonic transducer mounted to a backing substrate, wherein the backing substrate comprises a polymeric material having an acoustical attenuation that increases by at least about 2 dB/mm when the temperature of the backing substrate increases from about 5° C. to 40° C.

* * * * *